(12) United States Patent
Takimoto

(10) Patent No.: US 9,446,160 B2
(45) Date of Patent: Sep. 20, 2016

(54) CHLORINE DIOXIDE GAS GENERATOR

(71) Applicant: TAKIMOTOGIKEN KOGYO CO., LTD., Nagoya (JP)

(72) Inventor: Masateru Takimoto, Nagoya (JP)

(73) Assignee: TAKIMOTOGIKEN KOGYO CO., LTD, Nagoya (JP)

( * ) Notice: Subject to any disclaimer, the term of this patent is extended or adjusted under 35 U.S.C. 154(b) by 74 days.

(21) Appl. No.: 14/642,883

(22) Filed: Mar. 10, 2015

(65) Prior Publication Data

US 2015/0273096 A1 Oct. 1, 2015

(30) Foreign Application Priority Data

Mar. 26, 2014 (JP) ................. 2014-063873

(51) Int. Cl.
*A61L 2/20* (2006.01)
*C01B 11/02* (2006.01)

(52) U.S. Cl.
CPC ................ *A61L 2/20* (2013.01); *C01B 11/024* (2013.01)

(58) Field of Classification Search
CPC .............................. C01B 11/024; A61L 2/20
USPC .......................................... 422/187; 210/760
See application file for complete search history.

(56) References Cited

U.S. PATENT DOCUMENTS

| | | | |
|---|---|---|---|
| 2,916,527 A * | 12/1959 | Adams ..................... C07C 17/10 159/18 |
| 4,456,510 A | 6/1984 | Murakami et al. | |
| 2003/0229422 A1 * | 12/2003 | Martens ................ C01B 11/024 700/266 |
| 2009/0246074 A1 * | 10/2009 | Nelson ..................... A61L 2/20 422/29 |
| 2011/0052480 A1 * | 3/2011 | Martens ................ C01B 11/024 423/477 |

FOREIGN PATENT DOCUMENTS

| | | |
|---|---|---|
| GB | 2004475 A | 4/1979 |
| GB | 2146912 A | 5/1985 |
| JP | 4942643 | 11/1974 |
| JP | 53050716 | 4/1979 |
| JP | 54-153468 U | 10/1979 |
| JP | 58121442 | 3/1985 |
| JP | 1998182106 A | 7/1998 |
| JP | 2010207539 A | 9/2010 |

OTHER PUBLICATIONS

Japan Patent Office. Notification of Reasons of Refusal for Patent Application No. 2014-063873 dated Jun. 2, 2014 (English translation).

* cited by examiner

*Primary Examiner* — Huy-Tram Nguyen
(74) *Attorney, Agent, or Firm* — Trego, Hines & Ladenheim, PLLC

(57) ABSTRACT

A chlorine dioxide gas generator including a frame body which houses a first chemical tank which is filled with a first chemical containing chlorite, a second chemical tank which is filled with a second chemical containing acid, a reactor which causes a reaction between the first chemical containing chlorite and the second chemical containing acid, and a separation tank which separates a chlorine dioxide gas from a chlorine dioxide solution generated in the reactor, the chlorine dioxide gas generator being adapted to disinfect an enclosed space by means of the chlorine dioxide gas.

2 Claims, 13 Drawing Sheets

CHLORINE DIOXIDE GAS GENERATOR

BACKGROUND OF THE INVENTION

1. Field of the Invention

The present invention relates to chlorine dioxide generators for disinfecting enclosed spaces, and in particular, relates to a chlorine dioxide generator which performs disinfection by means of chlorine dioxide gas.

2. Description of the Related Art

Various kinds of fumigation devices that use chlorine dioxide gas have been proposed for example in Japanese Unexamined Patent Application Publication No. 1998-182106 and in Japanese Unexamined Patent Application Publication No. 2010-207539, and various solutions to the disadvantages of the use of chlorine dioxide gas have been developed. Typical disadvantages of the use of chlorine dioxide gas are listed below:
(a) Since chlorine dioxide gas is unstable and may explode, it must be used with caution for short periods of time.
(b) Chlorine dioxide gas cannot be stored for a long time, and therefore needs to be generated at the site of use.
(c) When a first chemical containing chlorite and a second chemical containing an acid react with each other, chlorine dioxide gas is generated as an aqueous solution. Therefore, in order to use the gas for fumigation, it must first be separated from the solution.

The contents of Japanese Unexamined Patent Application Publication No. 1998-182106 and Japanese Unexamined Patent Application Publication No. 2010-207539 are incorporated herein by reference in their entirety.

SUMMARY OF THE INVENTION

Problems to be Solved by the Invention

JP1998-182106 describes an invention relating to a method and an apparatus for generating chlorine dioxide gas, which has an object of providing a method for simply and safely generating chlorine dioxide gas, capable of efficiently generating chlorine dioxide gas in order to carry out fumigation, and an apparatus for generating chlorine dioxide gas. As shown in FIG. 11, such a method and apparatus for generating chlorine dioxide gas may include, for example: "Stirring a mixed solution containing a nonvolatile organic acid solution, a chlorite solution and a chloride for improving chlorine dioxide-producing ability. This gas generator is equipped with a reaction vessel 1, an air pump 3, a vent pipe 6 which communicates with the air pump 3 and an air stone 7. The air stone 7 is immersed in the mixed solution and a sealable opening part 1a is formed at the top of the reaction vessel 1 at a position higher than the water level of the mixed solution."

In this way, the "method and apparatus for generating chlorine dioxide gas" described in JP1998-182106 is thought to be capable of "providing a method for simply and safely generating chlorine dioxide gas, capable of efficiently generating chlorine dioxide gas in order to carry out fumigation disinfection", thus solving the foregoing problems (a)-(c).

However, paragraph [0021] of JP1998-182106 discloses the following: "Specifically, the container filled with the above-mentioned liquid mixture and an agitator or a bubbling apparatus may be carried into the disinfection environment, where stirring or bubbling may be performed. Thus generated chlorine dioxide gas, which in the case of bubbling is concomitant with a bubbling gas, diffuses out of the reaction solution (inside of the disinfection environment), thus realizing the desired fumigation disinfection of the disinfection environment."

According to this description in conjunction with FIG. 11, it is understood that in the method and apparatus for generating chlorine dioxide gas described in JP1998-182106, there is a risk that chlorine dioxide gas will be generated before starting the bubbling process, such as when filling the container with the liquid mixture or when carrying the container into the disinfection environment.

JP2010-207539 proposes an "indoor processing method and processing apparatus" with an object of "to safely, efficiently, and easily generate a chlorine dioxide gas without causing explosion due to local raising of gas concentration in a place where the chlorine dioxide gas is required". As illustrated in FIGS. 12 and 13, "in the processing method for indoor deodorization and sterilization, at least one of sodium chlorite and acid in a solution containing the sodium chlorite and acid arranged in an open container is measured in an amount wherein the local concentration within the open container of the chlorine dioxide gas generated by the reaction of the sodium chlorite and acid is less than 10%, and the measured solution containing one of the sodium chlorite and acid is arranged within the container, and the solution is heated to 50-95° C. from outside the container, thus, the reaction is accelerated and the reaction is completed within a predetermined time".

In this way, the "indoor processing method and processing apparatus" of JP2010-207539 is thought to be capable of "safely, efficiently, and easily generating a chlorine dioxide gas without causing explosion due to local raising of gas concentration in a place where the chlorine dioxide gas is required", thus solving the foregoing problems (a)-(c).

However, in the method and apparatus of JP2010-207539, "the solution is heated to 50-95° C. from outside the container, thus, the reaction is accelerated". This necessitates a heating apparatus and a controller for said heating apparatus, which raises costs.

In short, regardless of whether three liquid types are used as in JP1998-182106 or two liquid types are used as in JP2010-207539, chlorine dioxide gas generation occurs to a sufficient extent at room temperature even without additional chemical or physical stimulus. Therefore, it is only necessary to take efficiency into account. However, in both of the above patent documents, it appears that the efficiency of the methods and apparatuses therein has not been given enough consideration.

In other words, concerning fumigation apparatuses using chlorine dioxide gas, in addition to the foregoing typical disadvantages (a)-(c), the following problems (d)-(f) must also be solved.
(d) In an apparatus for generating chlorine dioxide gas, the solution materials should be in a completely separated state, and chlorine dioxide gas must not be generated until the solution materials are made to react with each other.
(e) When the chlorine dioxide gas is to be generated, the gas generating reaction should be made to occur efficiently within a short period of time.
(f) When using a first chemical containing chlorite and a second chemical containing an acid, a concentrated aqueous solution of chlorine dioxide will be generated, and therefore the chlorine dioxide gas must be efficiently separated from the water.

Accordingly, the present invention was completed as a result of due consideration, with respect to these types of fumigation apparatuses that use chlorine dioxide gas, of how to efficiently generate chlorine dioxide gas within a short period of time without accidental leakage, and how to make the fumigation process easy to control.

As such, it is an object of the present invention to provide a chlorine dioxide gas generator of a simple construction that is capable of efficiently generating and gasifying chlorine dioxide within a short period of time without accidental leakage, and to make the fumigation process easy to control.

A second object of the present invention is to provide a chlorine dioxide gas generator of a simple construction that achieves the foregoing object, and which is capable of efficiently separating the chlorine dioxide gas from the water.

Means of Solving the Problems

In order to solve the aforementioned problems, the means employed by the invention according to claim 1 will be described using the reference numerals used in the description of the embodiments below:

"A chlorine dioxide gas generator 100 comprising a frame body which houses a first chemical tank 16a which is filled with a first chemical containing chlorite, a second chemical tank 16b which is filled with a second chemical containing acid, a reactor 10 which causes a reaction between the first chemical containing chlorite and the second chemical containing acid, and a separation tank 20 which separates a chlorine dioxide gas 30b from a chlorine dioxide solution 30a generated in the reactor 10, the chlorine dioxide gas generator 100 being adapted to disinfect an enclosed space 40 by means of the chlorine dioxide gas 30b, wherein the reactor 10 comprises respectively large, medium, and small cylinders 11, 12, and 13 having bottom surfaces, a first spiral groove 14a between the large cylinder 11 and the medium cylinder 12, a second spiral groove 14b between the medium cylinder 12 and the small cylinder 13, and a lid 15 mounted to the large cylinder 11 which sequentially houses the medium cylinder 12 and the small cylinder 13, wherein both of the chemicals supplied to the bottom of the large cylinder 11 are made to react with each other as they are supplied in order to the first spiral groove 14a, the second spiral groove 14b, and a center cavity 13a of the small cylinder 13 so that the chlorine dioxide solution 30a can be generated, wherein the separation tank 20 comprises a plurality of vertically arranged gas discharge chambers 21, drain pipes 22 provided between the mutually adjacent gas discharge chambers 21, a liquid supply pipe 23 which supplies the chlorine dioxide solution 30a from the reactor 10 to the uppermost gas discharge chamber 21, and an air supply pipe 24 which feeds air into each of the gas discharge chambers 21, and wherein while the chlorine dioxide solution 30a flows from the liquid supply pipe 23 through the drain pipes 22 into each gas discharge chamber 21, air is fed into each gas discharge chamber 21 from the air supply pipe 24, and the chlorine dioxide gas 30b is separated into the air within each gas discharge chamber 21."

To summarize, the chlorine dioxide gas generator 100 according to claim 1 includes a first chemical tank 16a which is filled with a first chemical containing chlorite, a second chemical tank 16b which is filled with a second chemical containing acid, a reactor 10 which causes a reaction between the first chemical containing chlorite and the second chemical containing acid, and a separation tank 20 which separates a chlorine dioxide gas 30b from a chlorine dioxide solution 30a generated in the reactor 10, all housed within a frame body, and can release the chlorine dioxide gas 30b in an enclosed space 40, for example a factory, an office building, or an ordinary house, in order to disinfect the enclosed space 40. There are two types of this chlorine dioxide gas generator 100: A direct type which directly emits the chlorine dioxide gas 30b within the enclosed space 40 as shown on the left side of FIG. 1 (the generator being located inside the building), and a feed type which utilizes the air of the enclosed space 40 to dilute the chlorine dioxide gas 30b, and feeds the resultant diluted chlorine dioxide gas 30b into the enclosed space 40 as shown on the right side of FIG. 1 (the generator being located outside the building). The direct type chlorine dioxide gas generator 100 is shown in FIG. 2, and the feed type chlorine dioxide generator is shown in FIGS. 3 and 4.

As shown in FIGS. 6 and 7, the reactor 10, which makes the first chemical containing chlorite and the second chemical containing acid react with each other, includes the large cylinder 11 in the shape of a cylinder having a bottom surface, which makes up the external shape of the reactor 10, the medium cylinder 12 which is also in the shape of a cylinder having a bottom surface and housed within the large cylinder 11, and the small cylinder 13 which is also in the shape of a cylinder having a bottom and housed within the medium cylinder 12. As shown in FIG. 6, the first spiral groove 14a is formed between the large cylinder 11 and the medium cylinder 12, and the second spiral groove 14b is formed between the medium cylinder 12 and the small cylinder 13. As shown in FIG. 7, the lid 15 is mounted to the large cylinder 11 which sequentially houses the medium cylinder 12 and the small cylinder 13, the lid 15 securing the medium cylinder 12 and the small cylinder 13 within the large cylinder 11.

What is meant by the first spiral groove 14a being formed between the large cylinder 11 and the medium cylinder 12 is that the first spiral groove 14a is defined as an independent space by the large cylinder 11 and the medium cylinder 12. This independent space may of course be defined in the outer surface of the medium cylinder 12 as in the embodiment illustrated in FIG. 6, in the inner surface of the large cylinder 11, or spanning the boundary portions of the inner surface of the large cylinder 11 and the outer surface of the medium cylinder 12. In other words, the first spiral groove 14a may be formed either only in the inner surface of the large cylinder 11, only in the outer surface of the medium cylinder 12, or spanning both the inner surface of the large cylinder 11 and the outer surface of the medium cylinder 12. The same is true for the second spiral groove 14b with respect to the relationship of the medium cylinder 12 and the small cylinder 13.

As shown in FIGS. 2-4, the chemicals in the first chemical tank 16a and the second chemical tank 16b are separately fed to the reactor 10 through the chemical transporting pumps 16c, and are respectively supplied to a first connection port 11a and a second connection port 11b of the large cylinder 11, as shown in FIG. 6. In other words, the chemicals in the first chemical tank 16a and the second chemical tank 16b are contained separately respectively in the first chemical tank 16a and the second chemical tank 16b, and thus will not accidentally react with each other before they are supplied to the reactor 10.

When the chemicals in the first chemical tank 16a and the second chemical tank 16b are supplied through the chemical transporting pumps 16c to the connection ports 11a and 11b of the large cylinder 11, the chemicals enter the large cylinder 11 through holes formed in the bottom of the large cylinder 11, and a first mixing step is carried out in collectors 12*a* of the medium cylinder 12 housed within the large cylinder 11. After this, the chemicals flow through an outlet 12*b* which communicates with the bottom portion of the medium cylinder 12 and enter the first end of the first spiral groove 14*a*. The chemicals are then guided by the first spiral groove 14*a* to flow towards the second end of the first spiral groove 14*a*. Since the first spiral groove 14*a* literally is a groove with a spiral shape, it can for example have a total length several times the height of the large cylinder 11. The first spiral groove 14*a* carries out a second mixing step of the inflowing chemicals. The first and second mixing steps cause a reaction of the chemicals, starting generation of a given amount of chlorine dioxide solution 30*a*.

When the chemicals containing the chlorine dioxide solution 30*a* have flowed to the second end of the first spiral groove 14*a*, they enter the medium cylinder 12 through a communication port 12*c* formed at the second end of the first spiral grove 14*a*, and flow into the first end of the second spiral groove 14*b* formed on the surface of the small cylinder 13 which is housed within the medium cylinder 12. Then, the chemicals including the chlorine dioxide solution 30*a* flow through the second spiral groove 14*b* towards its second end (the lower end in this embodiment) and a third mixing step is carried out, whereby more chlorine dioxide solution 30*a* is generated from the remaining chemicals.

When the chemicals containing the chlorine dioxide solution 30*a* (at this stage the chemicals have almost completed their reaction and can be considered to completely consist of chlorine dioxide solution 30*a*) have reached the second end of the second spiral groove 14*b*, they will reach the lower end of a center cavity 13*a* through a connection port 13*b* formed at the lower end of the small cylinder 13, rise up through the center cavity 13*a* while undergoing further mixing, and then be discharged through the outlet 15*a* of the lid 15. At this time, the chemicals have completely become the chlorine dioxide solution 30*a*.

As a result, generation of the chlorine dioxide solution 30*a* in the reactor 10 will not occur unless the chemicals are fed into the small space constituting this reactor 10, which means that not only will there not be any accidental generation of the chlorine dioxide gas 30*b*, but also that by controlling the feeding of the chemicals, the amount of gas and time of generation can be controlled. Due to the presence of this reactor 10, the chlorine dioxide gas generator 100 according to the present invention can be made much smaller and compact than for example the apparatus proposed in JP1998-182106. The generated chlorine dioxide solution 30*a* is transported from the outlet 15*a* of the lid 15, which seals the interior of the reactor 10, to a separation tank 20 through a hose or the like, and the chlorine dioxide gas 30*b* is separated in this separation tank 20.

The chlorine dioxide solution 30*a* generated in the aforementioned reactor 10 is transported from the outlet 15*a* of the lid 15, which seals the reactor 10, to the separation tank 20 through a hose or the like, and the chlorine dioxide gas 30*b* is separated in this separation tank 20. In a chlorine dioxide gas generator 100 of the direct type illustrated in FIG. 2, the separated chlorine dioxide gas 30*b* is sprayed, as indicated by the arrows in the figure, into the enclosed space 40 in which the chlorine dioxide gas generator 100 is installed. In a chlorine dioxide gas generator 100 of the feed type illustrated in FIGS. 3 and 4, air either from the enclosed space 40 or from outside is blown by the blower fan 50 to dilute the chlorine dioxide gas 30*b* and spray it into the enclosed space 40.

Accordingly, the chlorine dioxide gas generator 100 according to claim 1 exhibits the following functions:

(a) Chlorine dioxide gas can be used within a short period of time.
(b) Chlorine dioxide gas can be generated at the site of use.
(c) Chlorine dioxide gas can be separated from water.
(d) Chlorine dioxide gas is not accidentally generated.
(e) Chlorine dioxide gas can be efficiently generated within a short period of time.

In the chlorine dioxide gas generator 100 according to the present invention, there is no accidental leakage of chlorine dioxide gas, chlorine dioxide can be generated and gasified within a short period of time and in an efficient manner, and the fumigation process can be more easily controlled.

Further, in the chlorine dioxide gas generator 100 according to the present invention, the separation tank 20 includes a plurality of vertically arranged gas discharge chambers 21, drain pipes 22 provided between the mutually adjacent gas discharge chambers 21, a liquid supply pipe 23 which supplies the chlorine dioxide solution 30*a* from the reactor 10 to the uppermost gas discharge chamber 21, and an air supply pipe 24 which feeds air into each of the gas discharge chambers 21. While the chlorine dioxide solution 30*a* flows from the liquid supply pipe 23 through the drain pipes 22 into each gas discharge chamber 21, air is fed into each gas discharge chamber 21 from the air supply pipe 24, and the chlorine dioxide gas 30*b* is separated into the air within each gas discharge chamber 21.

In the chlorine dioxide gas generator 100 according to claim 1, the separation tank 20 is compact and efficient, and easily allows for the chlorine dioxide gas generator 100 to be modified to a direct type or a feed type gas generator. As shown in FIGS. 8-10, the separation tank 20 has a plurality of gas discharge chambers 21 arranged vertically, and an air supply pipe 24 which passes through the center of the gas discharge chambers 21 and through which air can be fed into each of the gas discharge chambers 21.

As shown in FIGS. 8-10, in the separation tank 20, a liquid supply pipe 23 is connected to the uppermost gas discharge chamber 21, the liquid supply pipe 23 supplying the gas discharge chambers 21 with the chlorine dioxide solution 30*a* from the reactor 10, drain pipes 22 are provided between each of the gas discharge chambers 21, and the chlorine dioxide solution 30*a* which has been supplied to the uppermost gas discharge chamber 21 through the liquid supply pipe 23 flows downward to the lower gas discharge chambers 21. In the embodiment described below, there are five gas discharge chambers 21, and separation of chlorine dioxide gas 30*b* from the chlorine dioxide solution 30*a* can be performed in each of the gas discharge chambers 21. Through experimentation, the inventor has found that three gas discharge chambers 21 are sufficient to perform the separation.

Each drain pipe 22 serves to maintain a fixed depth of chlorine dioxide solution 30*a* in each gas discharge chamber 21, ensuring that the stimulus of the air from the air supply pipe 24 reaches all of the gas discharge chambers 21, and that chlorine dioxide gas 30*b* can be sufficiently separated from the chlorine dioxide solution 30*a*, while maintaining a constant downward flow rate of the chlorine dioxide solution 30*a* towards the lower gas discharge chambers 21.

Gas outlets 25 are formed in the upper portions of the sidewalls of each gas discharge chamber 21 in order to discharge the chlorine dioxide gas 30*b* from the gas discharge chambers 21. A chlorine dioxide gas generator 100 having the separation tank illustrated in FIG. 8, which has these gas outlets 25 open directly into an enclosed space such as the one shown in FIG. 1, will be of the direct type. Conversely, as illustrated in FIG. 10, by enclosing the periphery of the gas discharge chambers 21 with an air duct cover 51 and feeding air into the air duct cover 51 by means of a blower fan 50, the chlorine dioxide gas generator 100 will be of the feed type, which dilutes the chlorine dioxide gas 30b.

Accordingly, in addition to the above functions (a)-(e), the chlorine dioxide gas generator 100 according to claim 1 exhibits the following functions:

(f) The chlorine dioxide gas can be separated from the water.
(g) The separation of the chlorine dioxide gas from the water can be performed in an efficient manner.

The chlorine dioxide gas generator 100 provides these functions with a simple construction.

Further, in order to solve the aforementioned problems, claim 2 adds the following feature to the chlorine dioxide gas generator 100 according to claim 1: "A blower fan which forcibly feeds air from the enclosed space or outside air into the chlorine dioxide gas separated by the separation tank so as to dilute the chlorine dioxide gas."

The chlorine dioxide gas generator 100 according to claim 2 particularly regards a feed type generator according to claim 1. As shown in FIGS. 3 and 4, the generator according to claim 2 is equipped with a blower fan 50 which forcibly supplies air from the enclosed space 40 or from outside in order to dilute the chlorine dioxide gas.

In the chlorine dioxide gas generator 100 shown in FIG. 3, the blower fan 50 is provided in an air duct cover 51 which covers the chlorine dioxide gas rising from the separation tank 20, and which has a suction port and a discharge port which open to the enclosed space 40. The blower fan 50 dilutes the chlorine dioxide gas 30b by sucking in air from the enclosed space 40 and directing this air towards the rising chlorine dioxide gas 30b. The chlorine dioxide gas 30b having been diluted by this air is then discharged through the discharge port into the enclosed space 40.

In the chlorine dioxide gas generator 100 shown in FIG. 4, the blower fan 50 is arranged on the right-hand side of the reactor 10, and sucks in air from the enclosed space 40 or from outside through a hose (not shown), and then feeds this air into the separation tank 20. This configuration is intended to be the generator shown on the right side (outside the building) in FIG. 1.

The separation tank 20 shown in FIG. 4 has a structure as shown in for example FIG. 10, wherein air from the blower fan 50 is fed into the air duct cover 51 which covers the entire outside of the separation tank 20, whereby the chlorine dioxide gas 30b emitted from the separation tank 20 is diluted. Further, a large supply tube 52 and a small supply tube 53 are connected to the air duct cover 51 shown in FIG. 10. The large supply tube 52 corresponds to the hose at the top side of the chlorine dioxide gas generator 100 shown in FIG. 1.

Accordingly, in addition to exhibiting similar functions to those of claim 1, the chlorine dioxide gas generator 100 according to claim 2 is of the feed type since it is equipped with the blower fan 50. With the feed type chlorine dioxide gas generator, it is easier to adjust the concentration of the chlorine dioxide gas 30b compared to the direct type.

Effects of the Invention

As described above, the main structural features of the present invention are as follows:

"A chlorine dioxide gas generator 100 comprising a frame body which houses a first chemical tank 16a which is filled with a first chemical containing chlorite, a second chemical tank 16b which is filled with a second chemical containing acid, a reactor 10 which causes a reaction between the first chemical containing chlorite and the second chemical containing acid, and a separation tank 20 which separates a chlorine dioxide gas 30b from a chlorine dioxide solution 30a generated in the reactor 10, the chlorine dioxide gas generator 100 being adapted to disinfect an enclosed space 40 by means of the chlorine dioxide gas 30b, wherein the reactor 10 comprises respectively large, medium, and small cylinders 11, 12, and 13 having bottom surfaces, a first spiral groove 14a between the large cylinder 11 and the medium cylinder 12, a second spiral groove 14b between the medium cylinder 12 and the small cylinder 13, and a lid 15 mounted to the large cylinder 11 which sequentially houses the medium cylinder 12 and the small cylinder 13, wherein both of the chemicals supplied to the bottom of the large cylinder 11 are made to react with each other as they are supplied in order to the first spiral groove 14a, the second spiral groove 14b, and the center cavity 13a of the small cylinder 13 so that the chlorine dioxide solution 30a can be generated, wherein the separation tank 20 comprises a plurality of vertically arranged gas discharge chambers 21, drain pipes 22 provided between the mutually adjacent gas discharge chambers 21, a liquid supply pipe 23 which supplies the chlorine dioxide solution 30a from the reactor 10 to the uppermost gas discharge chamber 21, and air supply pipe 24 which feeds air into each of the gas discharge chambers 21, and wherein while the chlorine dioxide solution 30a flows from the liquid supply pipe 23 through the drain pipes 22 into each gas discharge chamber 21, air is fed into each gas discharge chamber 21 from the air supply pipe 24, and the chlorine dioxide gas 30b is separated into the air within each gas discharge chamber 21."

Due to these features, it is possible to provide a chlorine dioxide gas generator 100 of a simple construction, in which there is no accidental leakage of the chlorine dioxide gas 30b, chlorine dioxide can be efficiently generated and gasified within a short period of time, and the fumigation process is easy to control.

DESCRIPTION OF THE EMBODIMENTS

Figure 1:
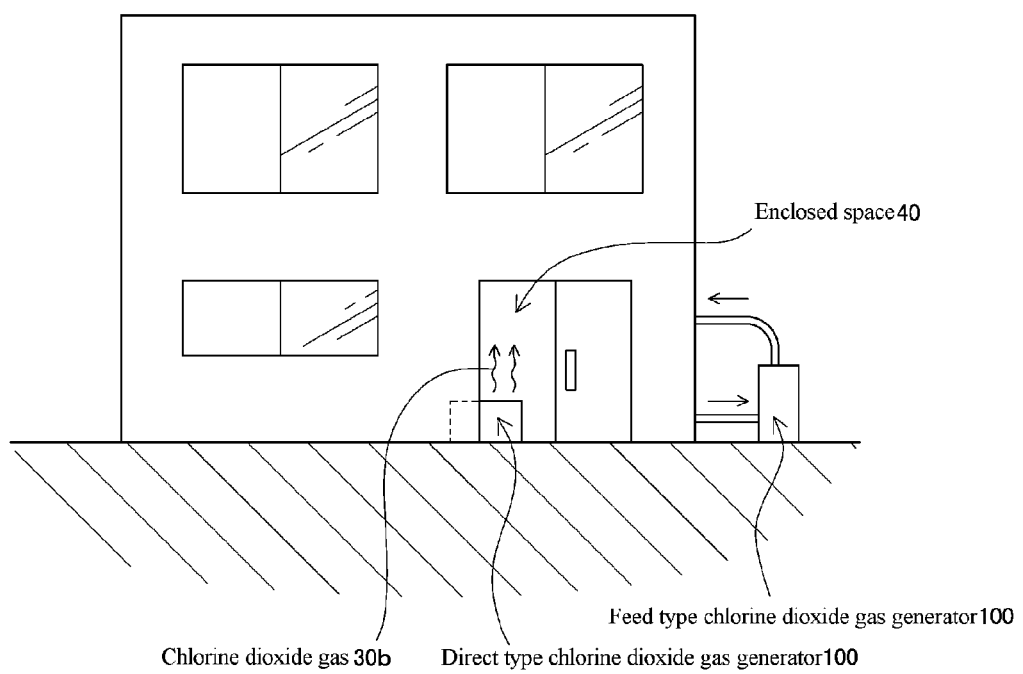
FIG. 1 is a front view of an enclosed space 40 showing fumigation of the interior of the enclosed space 40 being performed using the chlorine dioxide gas generator 100 according to the present invention.

The invention according to the claims and having the aforementioned construction will now be described with reference to the embodiments of the chlorine dioxide gas generator 100 shown in the drawings. As shown in FIG. 1, the chlorine dioxide gas generator 100 emits the chlorine dioxide gas 30b in an enclosed space 40 such as a factory, an office building, or an ordinary house, and disinfects the enclosed space 40 by means of the chlorine dioxide gas 30b. As shown in FIGS. 2-5, the chlorine dioxide gas generator 100 includes a frame body which houses a first chemical tank 16a which is filled with a first chemical containing chlorite, a second chemical tank 16b which is filled with a second chemical containing acid, a reactor 10 which causes a reaction between the first chemical containing chlorite and the second chemical containing acid, and a separation tank 20 which separates a chlorine dioxide gas 30b from a chlorine dioxide solution 30a generated in the reactor 10, the chlorine dioxide gas generator 100 being adapted to disinfect an enclosed space 40 by means of the chlorine dioxide gas 30b.

Figure 3:
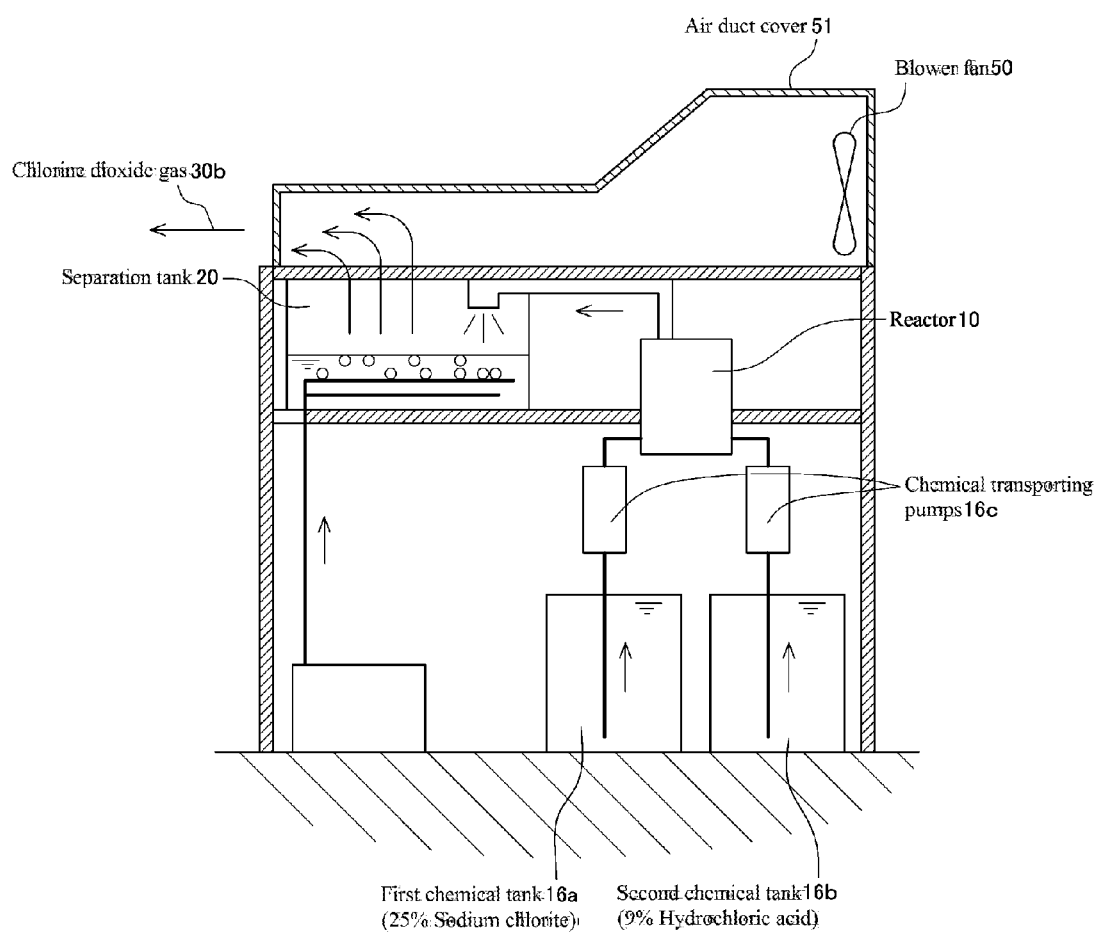
FIG. 3 is a schematic structural drawing showing a feed type chlorine dioxide generator 100.
Figure 4:
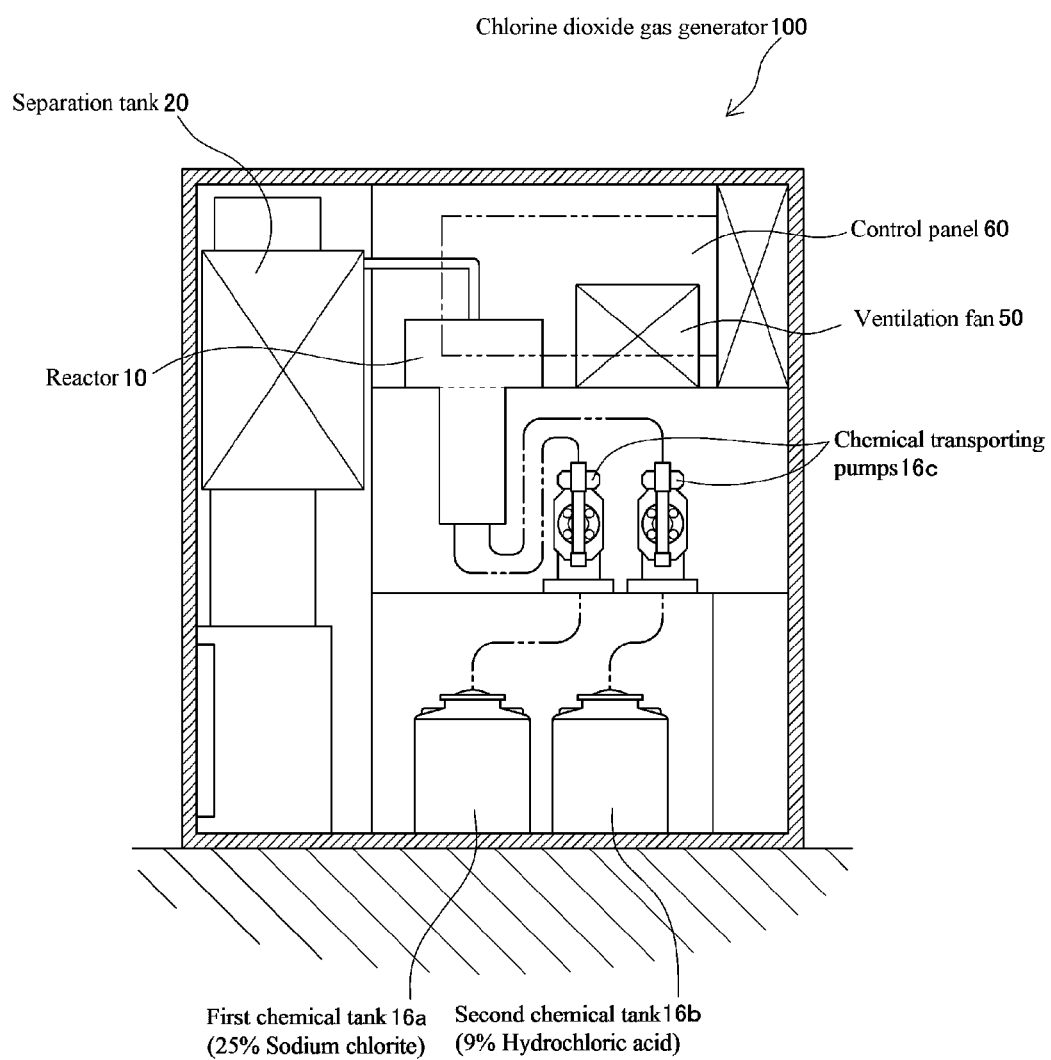
FIG. 4 is a front view showing the overall structure of another embodiment of the feed type chlorine dioxide gas generator 100.

There are two types of embodiments of the chlorine dioxide gas generator 100; a direct type as shown on the left side of FIG. 1, which directly emits the chlorine dioxide gas 30b inside the enclosed space 40, and a feed type as shown on the right side of FIG. 1 (installed outside the building), which uses air from inside the enclosed space 40 to dilute the chlorine dioxide gas 30b and feeds the diluted chlorine dioxide gas 30b into the enclosed space 40. The direct type chlorine dioxide gas generator 100 is shown in FIG. 2, and the feed type chlorine dioxide gas generator 100 is shown in FIGS. 3 and 4.

Figure 2:
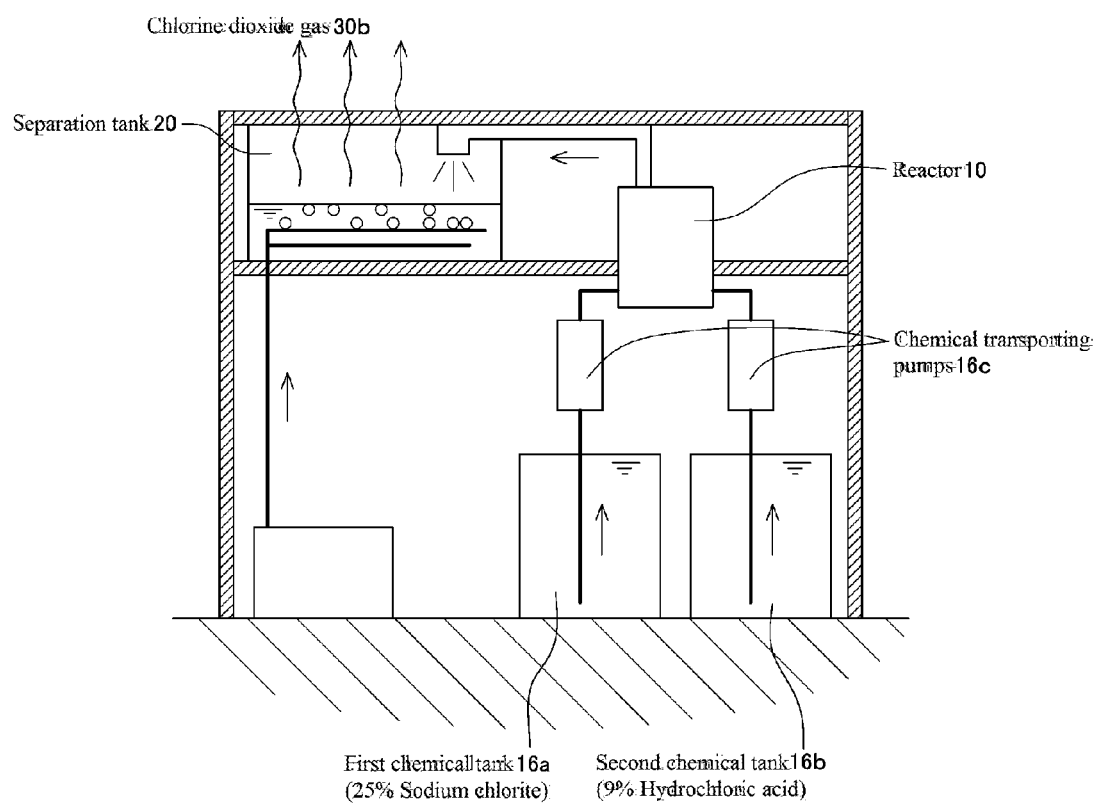
FIG. 2 is a schematic structural drawing showing a direct type chlorine dioxide generator 100.

The chlorine dioxide gas generator 100 shown in FIG. 2 includes a frame body which houses a first chemical tank 16a which is filled with a first chemical containing chlorite, a second chemical tank 16b which is filled with a second chemical containing acid, a reactor 10 which causes a reaction between the first chemical containing chlorite and the second chemical containing acid to generate a chlorine dioxide solution 30a, and a separation tank 20 which separates a chlorine dioxide gas 30b from the chlorine dioxide solution 30a generated in the reactor 10.

The first chemical tank 16a filled with for example 25% sodium chlorite and the second chemical tank 16b filled with for example 9% hydrochloric acid are each connected to the reactor 10 via separate chemical transporting pumps 16c. The chemicals are fed into the reactor 10 through operation of the chemical transporting pumps 16c, allowing the generation of chlorine dioxide solution 30a to begin. The chlorine dioxide solution 30a generated in the reactor 10 may then be fed into the separation tank 20 through pipes etc.

In the separation tank 20 as shown in FIG. 2, an air pump supplies air through an air hose into an air valve (corresponding to the air stone described in JP 1998-182106) inside the separation tank 20. This causes air bubbles which deal physical shocks to the chlorine dioxide solution 30a. Accordingly, when the chlorine dioxide solution 30a flows into the separation tank 20 and receives physical shocks from the air bubbles, chlorine dioxide gas 30b is separated from the chlorine dioxide solution 30a. Then, as shown by the arrows in FIG. 2, the chlorine dioxide gas 30b is emitted from an opening of the chlorine dioxide gas generator 100 directly into the enclosed space 40 in which the chlorine dioxide gas generator is installed.

The feed type chlorine dioxide gas generator 100 shown in FIG. 3 is the chlorine dioxide gas generator shown in FIG. 2 provided with an air duct cover 51 having a blower fan 50, and is adapted to use air to dilute the chlorine dioxide gas 30b rising from the separation tank 20. The blower fan 50 is provided within the air duct cover 51, which encloses the chlorine dioxide gas 30b rising from the separation tank 20 and has a suction port and a discharge port which communicate with the enclosed space 40, and dilutes the chlorine dioxide gas 30b rising from the separation tank 20 by sucking in air from the enclosed space 40 and blowing it towards the chlorine dioxide gas 30b. The air-diluted chlorine dioxide gas 30b is then discharged into the enclosed space 40 through the discharge port.

Figure 5:
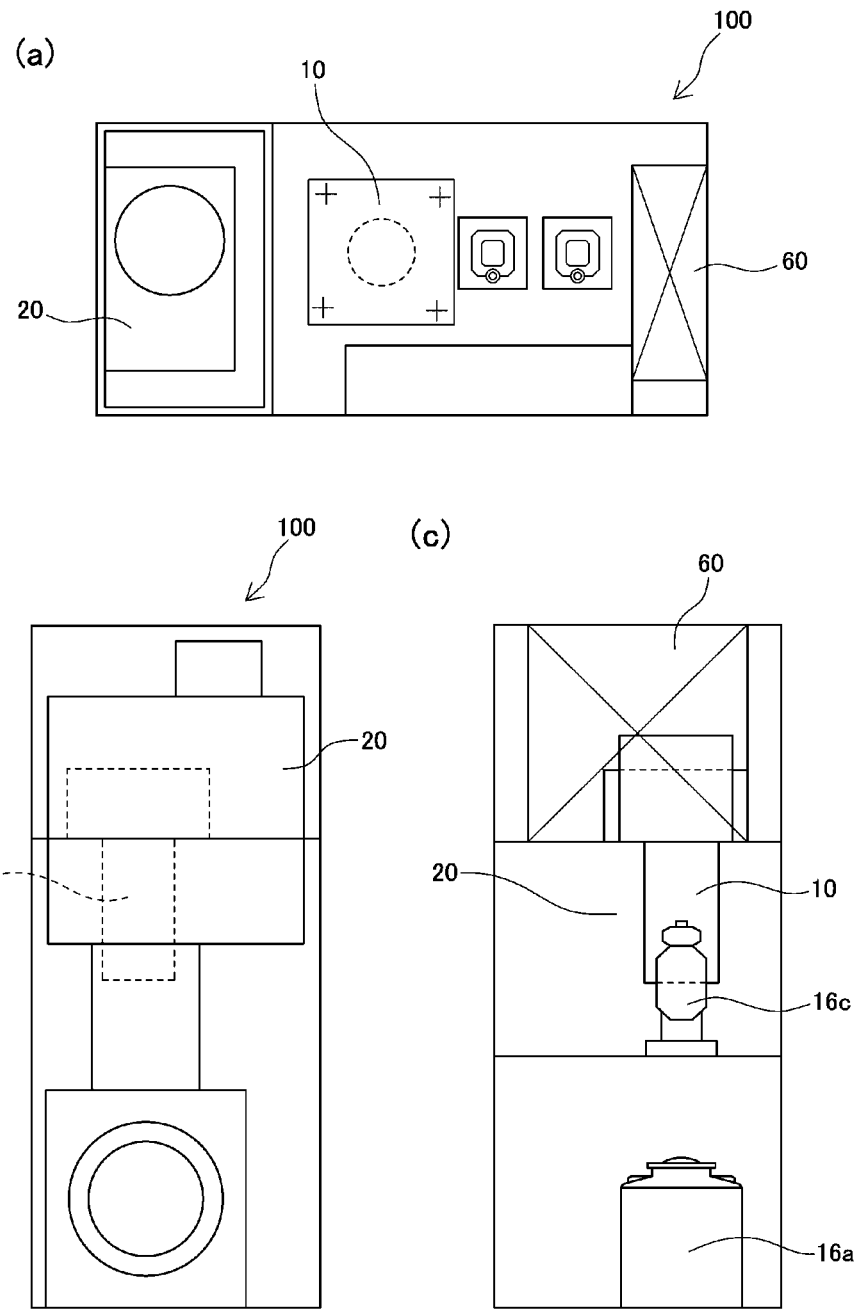
FIG. 5 shows the chlorine dioxide gas generator 100 shown in FIG. 4, in a plan view (a), a left side view (b), and a right side view (c).

The chlorine dioxide gas generator 100 shown in FIGS. 4 and 5 has the blower fan 50 provided separately from the separation tank 20, and can be adapted into either the direct type or the feed type, depending on the configuration of the separation tank 20. This chlorine dioxide gas generator 100 as shown in FIGS. 4 and 5 is intended to be installed outside a building as shown on the right side of FIG. 1, allowing the chlorine dioxide gas 30b separated in the separation tank 20 to be transported into the enclosed space 40 as is, or after being diluted using either air from the enclosed space 40 or outside air.

Figure 6:
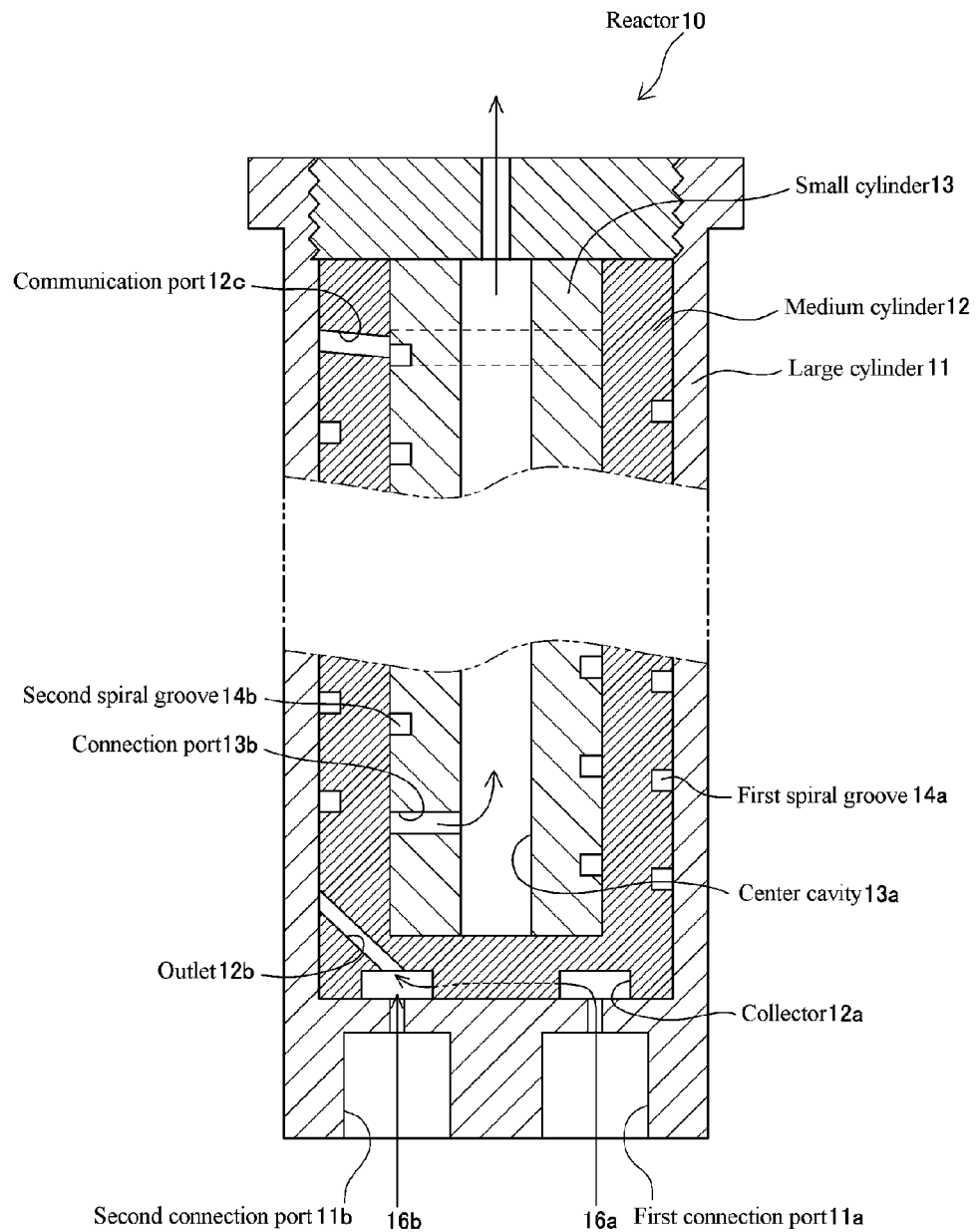
FIG. 6 is a schematic sectional view of the reactor 10 used in the chlorine dioxide gas generator 100.
Figure 7:
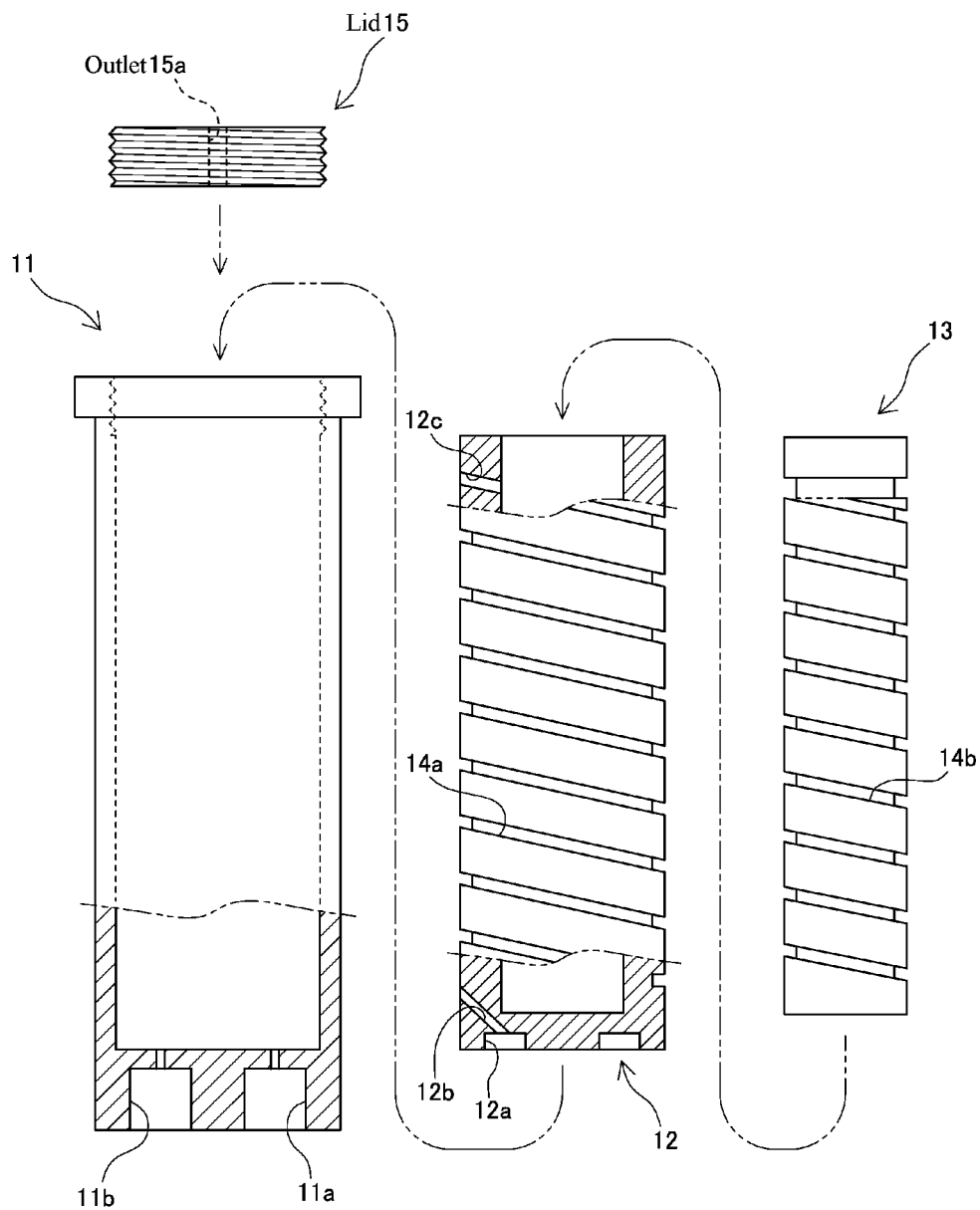
FIG. 7 is a front view showing sectional views of the disassembled components of the reactor 10.

FIGS. 6 and 7 show the reactor 10 used in the present embodiment of the chlorine dioxide gas generator 100. As shown in FIG. 7, the reactor 10 includes a large cylinder 11 having a bottom surface, which makes up the external shape of the reactor 10, a medium cylinder 12 having a bottom surface and housed within the large cylinder 11, and a small cylinder 13 having a bottom surface and housed within the medium cylinder 12. As shown in FIG. 6, a first spiral groove 14a is formed between the large cylinder 11 and the medium cylinder 12, and a second spiral groove 14b is formed between the medium cylinder 12 and the small cylinder 13. Also as shown in FIG. 6, a lid 15 is attached to the large cylinder 11 which houses the medium cylinder 12 and the small cylinder 13, the lid 15 securing the medium cylinder 12 and the small cylinder 13 within the large cylinder 11.

As shown in FIG. 7, the large cylinder 11 has a first connection port 11a and a second connection port 11b. The first chemical tank 16a and the second chemical tank 16b are individually connected to the chemical transporting pumps 16c, which are individually connected to the first and second connection ports 11a and 11b. The first connection port 11a and the second connection port 11b communicate with the inside of the large cylinder 11 through holes provided in the bottom portions of each of the first and second connection ports 11a and 11b. The large cylinder 11 also has a flange formed at its top portion in order to facilitate installation of the large cylinder in the chlorine dioxide gas generator 100.

As shown in FIG. 7, the medium cylinder 12 housed within the large cylinder 11 has a first spiral groove formed over the entirety of its outer peripheral surface, and has a collector 12a formed in its bottom surface. The collector 12a is an annular groove which communicates simultaneously with the first connection port 11a and the second connection port 11b of the large cylinder 11 regardless of in what manner the medium cylinder 12 is housed within the separation tank 20. An outlet 12b is also formed at the bottom portion of the medium cylinder 12 such that the inside of the collector 12a communicates with the first spiral groove 14a, and a communication port 12c is formed at the location of the medium cylinder 12 where the top portion of the first spiral groove 14a is located, such that the top of the first spiral groove 14a communicates with the inside of the medium cylinder 12.

As shown in FIG. 7, the small cylinder 13 housed within the medium cylinder 12 has a second spiral groove 14b formed over the entirety of its outer peripheral surface, and its interior makes up a center cavity 13a. The top portion of the second spiral groove 14b is an annular groove which runs around the periphery of the small cylinder 13. Therefore, regardless of the location of the communication port 12c on the medium cylinder 12 side, it will always be in communication with the second spiral groove 14b. A connection port 13b is formed at the bottom portion of the second spiral groove 14b such that the second spiral groove 14b communicates with the center cavity 13a of the small cylinder 13.

Looking now to the lid 15, this lid 15 has a screw thread cut into its perimeter, which lets the lid 15 secure the medium cylinder 12 and the small cylinder 13 within the large cylinder 11, by screwing the lid 15 into the top of the large cylinder 11. An outlet 15a is provided in the center of the lid, through which the chlorine dioxide solution 30a from the center cavity 13a of the small cylinder 13 can be transported to the separation tank 20 described below.

Figure 8:
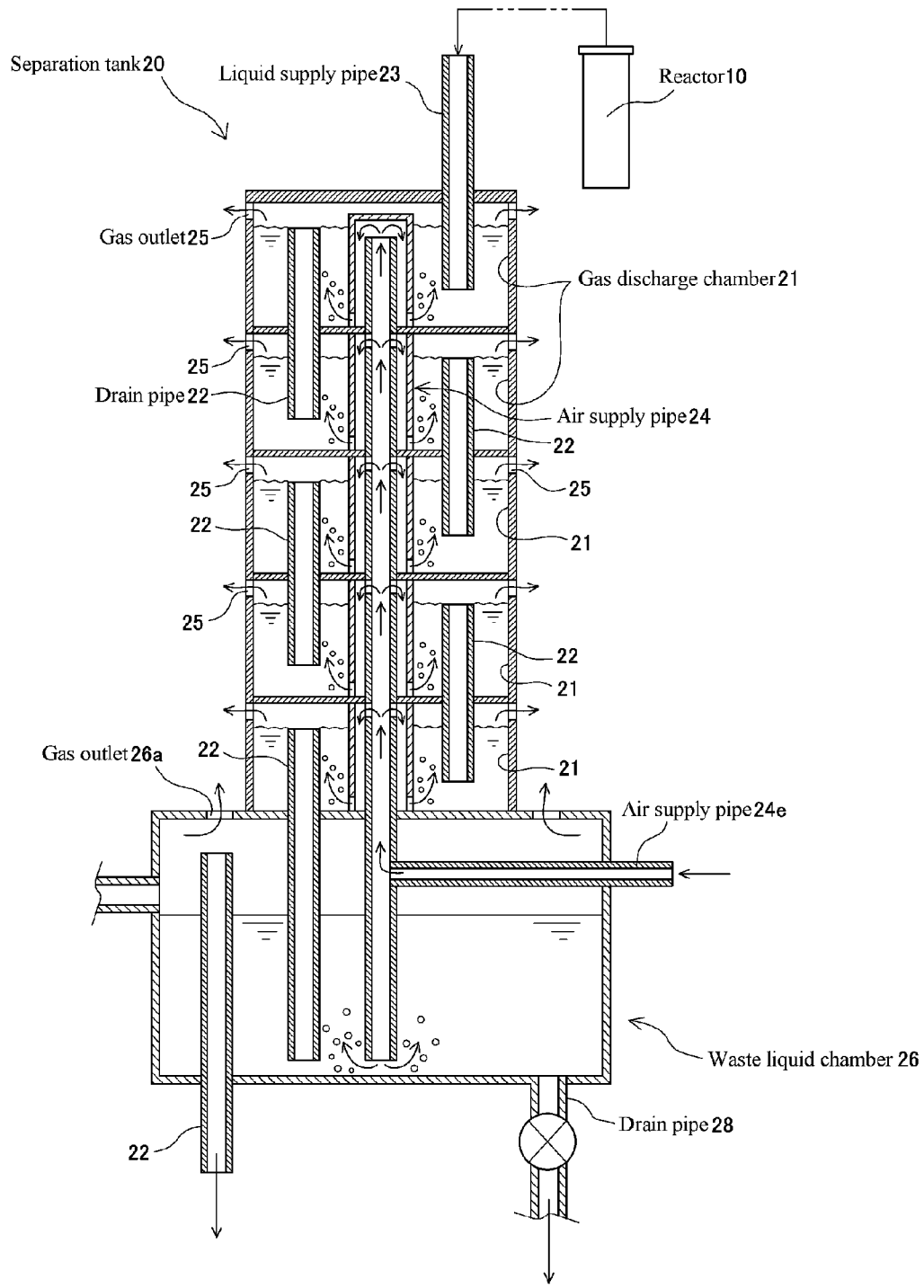
FIG. 8 is a longitudinal sectional view of the separation tank 20 used in the direct type chlorine dioxide gas generator 100.
Figure 9:
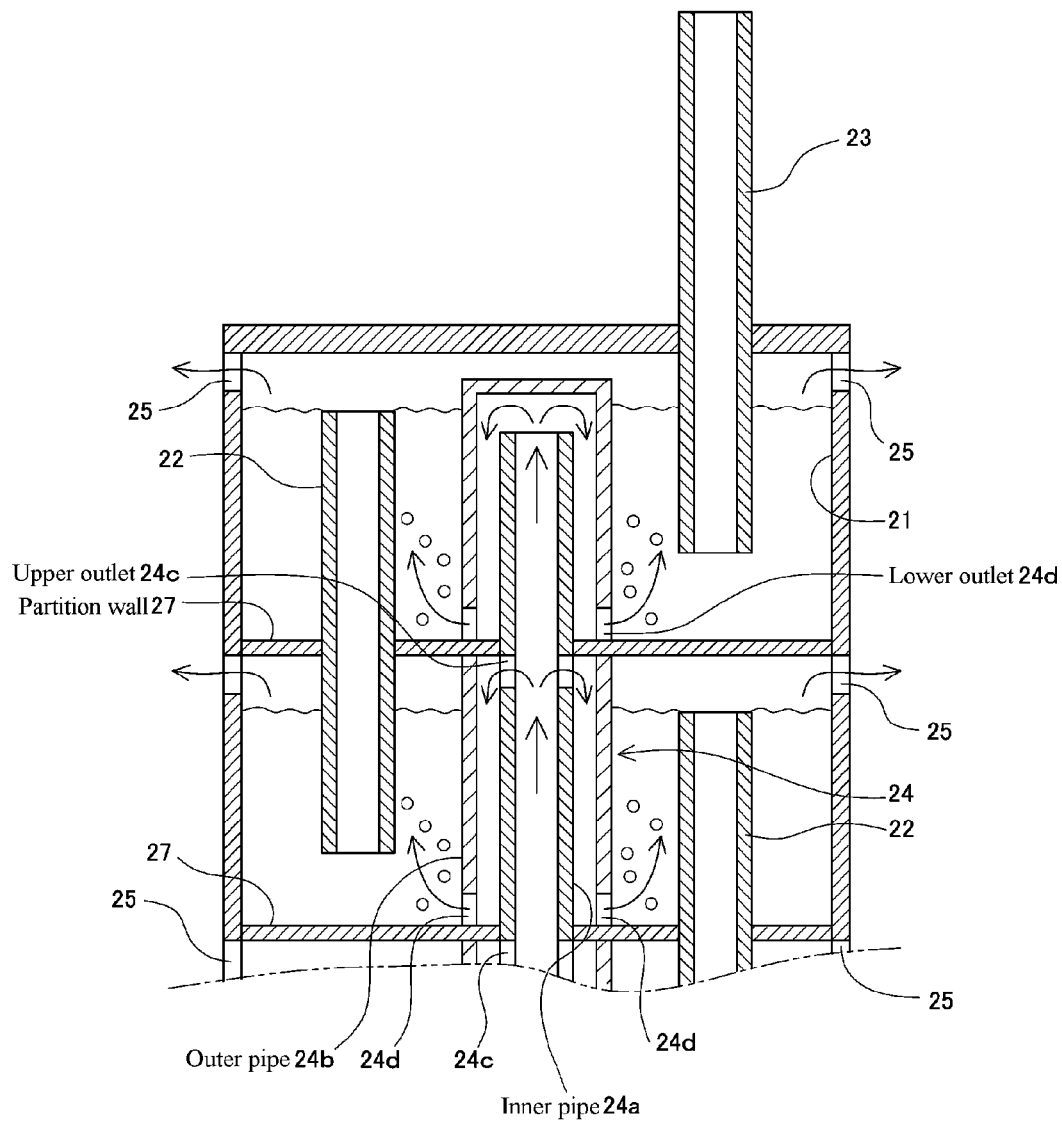
FIG. 9 is an enlarged sectional view of the upper portion of the separation tank shown in FIG. 8.
Figure 10:
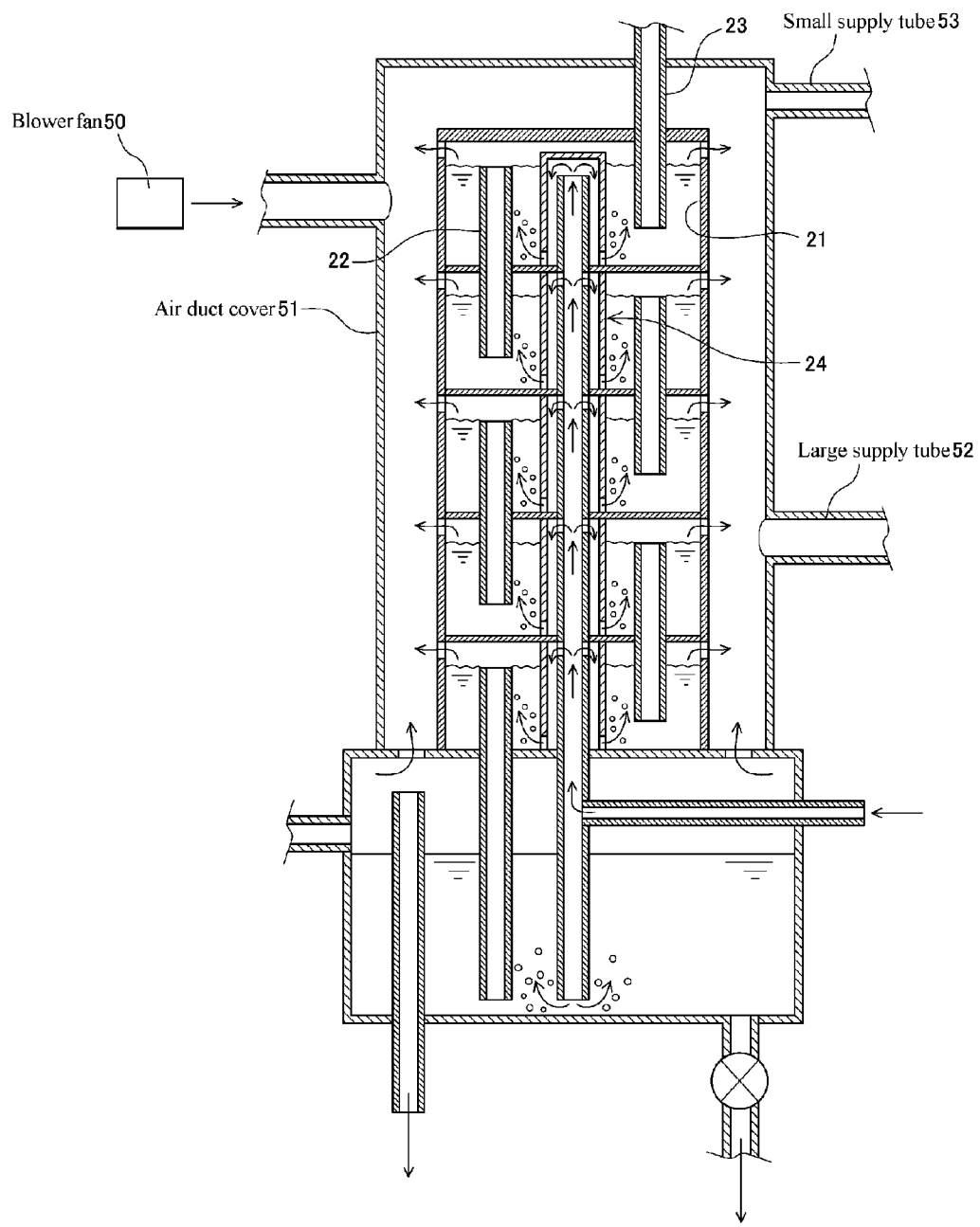
FIG. 10 is a longitudinal sectional view of the separation tank 20 used in the feed type chlorine dioxide gas generator 100.
Figure 11:
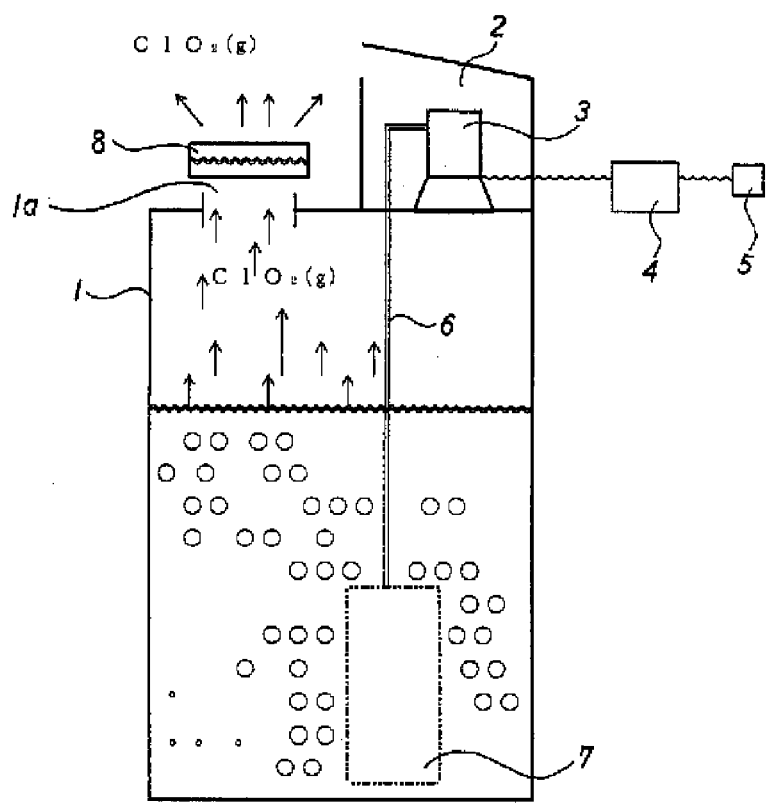
FIG. 11 is a sectional view of the apparatus proposed in JP1998-182106.
Figure 12:
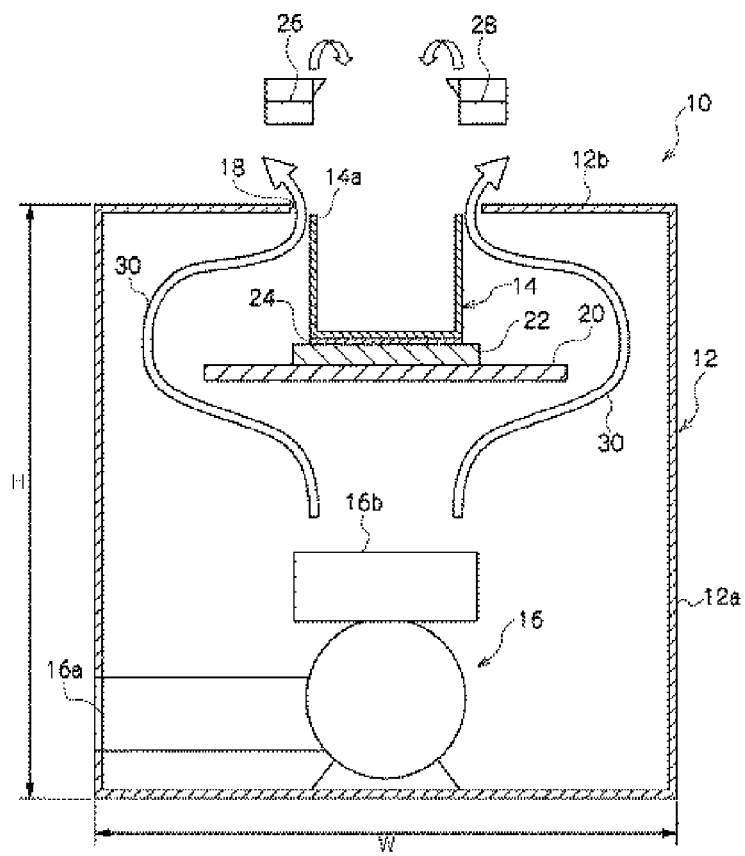
FIG. 12 is a sectional view of the apparatus proposed in JP2010-207539.
Figure 13:
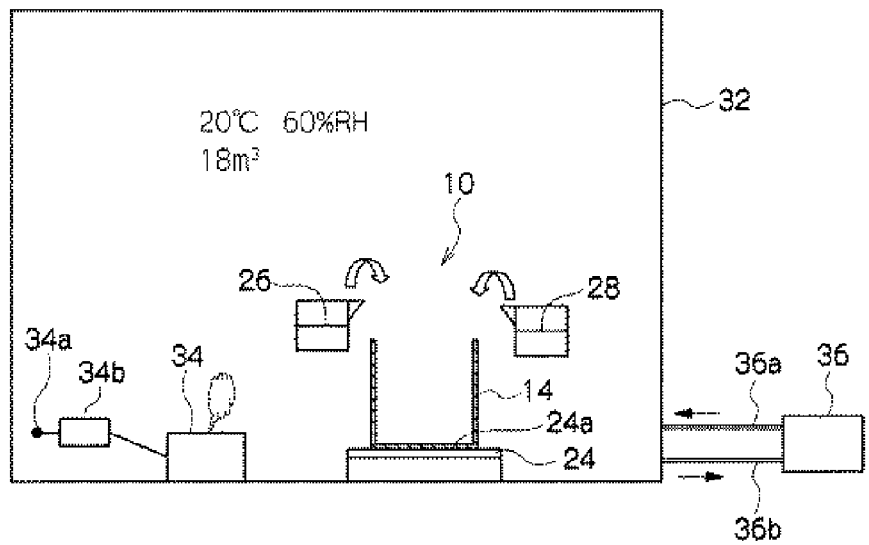
FIG. 13 is a sectional view showing fumigation being performed using the apparatus proposed in JP2010-207539.

FIGS. 8-10 show the separation tank used in the chlorine dioxide gas generator 100 according to the present embodiment of the invention, and is adapted such that the chlorine dioxide solution 30a from the aforementioned reactor 10 is supplied to the interior of the separation tank 20 through a liquid supply pipe 23. The separation tank 20 is composed of a plurality of vertically arranged gas discharge chambers 21, drain pipes 22 provided between the vertically adjacent gas discharge chambers 21, the liquid supply pipe 23 which supplies the chlorine dioxide solution 30a from the reactor 10 into the uppermost gas discharge chamber 21, and an air supply pipe 24 which feeds air into each of the gas discharge chambers 21.

As shown in FIGS. 8 and 10, the gas discharge chambers 21 are configured as boxes stacked vertically in the manner of a five-story building on top of a waste liquid chamber 26, the upper and lower boundaries between each chamber being defined by partition walls 27. In the upper portions of the side walls constituting each of the gas discharge chambers 21, gas outlets 25 are formed in order to discharge the chlorine dioxide gas 30b that has been separated from the chlorine dioxide solution 30a in the gas discharge chambers 21. As shown in FIG. 9, the liquid supply pipe 23 for transporting the chlorine dioxide solution 30a from the reactor 10 is connected to the uppermost gas discharge chamber 21.

The interiors of the gas discharge chambers 21 are sequentially connected via the drain pipes 22 which are vertically provided passing through the partition walls 27. Each drain pipe 22 is in the form of a tube open on both top and bottom ends, the top end communicates with the upper portion of the upper gas discharge chamber 21, and the bottom end communicates with the lower portion of the lower gas discharge chamber 21, such that the depth of the chlorine dioxide solution 30a in each gas discharge chamber 21 is kept constant, and the stimulus of the air from the air supply pipe 24 sufficiently permeates the chlorine dioxide solution 30a. By opening into the lower portion of the lower gas discharge chamber 21, each drain pipe 22 also maintains a constant downward flow rate of the chlorine dioxide solution 30a supplied from the liquid supply pipe 23 as it flows into the lower gas discharge chambers 21, while allowing for sufficient separation of chlorine dioxide gas 30b from the chlorine dioxide solution 30a in the gas discharge chamber 21. The drain pipe 22 in the lowest of the gas discharge chambers 21 communicates with the waste liquid chamber 26.

The air supply pipe 24 is provided passing through the gas discharge chambers 21, and feeds air into each of the gas discharge chambers 21. As shown in FIG. 9, the air supply pipe 24 is composed of an inner pipe 24a and an outer pipe 24b which form an empty space between each other. The inner pipe 24a has an opening at its top end, and has upper outlets 24c formed directly below the portions of the inner pipe 24a which connect with the partition walls 27. As shown in FIGS. 8 and 10, the bottom end of the inner pipe 24a communicates with the waste liquid chamber 26 provided at the bottom level, and an air supply pipe 24e is attached to the inner pipe 24a inside the waste liquid chamber 26 in order to supply outside air to the inner pipe 24a.

Meanwhile, as shown in FIG. 9, the top end of the outer pipe 24b is closed, and lower outlets 24d are formed directly above the portions of the outer pipe 24 which connect with the partition walls 27. The outer pipe 24b communicates with the bottom portion of the lowest gas discharge chamber 21.

In the separation tank 20 of the present embodiment of the invention, the lowest of the gas discharge chambers 21 is attached to the waste liquid chamber 26, as shown in FIGS. 8 and 10, and a drain pipe 28, similar to the ones provided in the gas discharge chambers 21, is provided in the waste liquid chamber 26. As mentioned above, the bottom ends of both the drain pipe 22 provided in the gas discharge chamber 21 directly above the waste liquid chamber 26 and the inner pipe 24a of the air supply pipe 24 pass through into the waste liquid chamber 26.

In summary, the salt water (waste liquid) remaining after the chlorine dioxide gas 30b has been separated in the gas discharge chambers 21 is collected in the waste liquid chamber 26, and is discharged through either the drain pipe 22 or the drain pipe 28 provided in the waste liquid chamber 26. Even supposing that there is chlorine dioxide remaining in the waste liquid that has been discharged into the waste liquid chamber 26, it will be completely separated in the waste liquid chamber 26 and discharged through the gas outlets 26a provided in the waste liquid chamber 26.

The separation tank 20 shown in FIG. 8 does not have the air duct cover 51 provided at its periphery. A chlorine dioxide gas generator 100 having this separation tank 20 will therefore be of the direct type. Conversely, in the separation tank 20 shown in FIG. 10, the gas discharge chambers 21 are covered by the air duct cover 51, and a blower fan 50 feeds air into the air duct cover 51, meaning that the chlorine dioxide generator 100 will be of the feed type, in which the chlorine dioxide gas 30b is diluted. As mentioned above, when configuring the chlorine dioxide gas generator 100 to be of the feed type, the blower fan 50 may be installed housed within the air duct cover 51, and a large supply tube 52 and a small supply tube 53 may be provided to the air duct cover 51.

In the chlorine dioxide gas generator 100 according to the present embodiment, the chemical transporting pumps 16c which supply chemicals to the first and second chemical tanks 16a and 16b, the air pump which feeds air through the air supply pipe 24e to the interior of the inner pipe 24a of the air supply pipe 24, and the blower fan 50, are controlled by a control panel 60 provided on a portion of the chlorine dioxide gas generator 100. In this case, control is effected by a control system based on received signals from a concentration sensor installed in the enclosed space 40 which senses the concentration of the chlorine dioxide solution 30a, or from a timer etc.

The chlorine dioxide gas generator 100 according to the foregoing embodiment will now be explained referring to a basic embodiment wherein in an enclosed space 40 having a capacity of 50 m$^3$, the concentration of the chlorine dioxide gas 30b is 400 ppm (desired concentration to enable fumigation). Further, the maximum allowable concentration of the chlorine dioxide gas 30b in an enclosed space having a capacity of 450 m$^3$ is twice the desired concentration; 800 ppm, and the amount of chlorine dioxide gas 30b needed to achieve this concentration is 1010 g. Based on these premises, the first chemical tank 16a may be filled with 4.5 liters (5.4 kg) of 25% sodium chlorite, and the second chemical tank 16b may be filled with 4.7 liters (4.8 kg) of 9% hydrochloric acid.

In other words, a capacity of 10 liters of the first and second chemical tanks 16a and 16b is sufficient in order to make the concentration of the chlorine dioxide gas 30b in an enclosed space 40 having a capacity of 450 m$^3$ be 400 ppm in the time described below. Further, since the reactor 10 which is supplied with chemicals from the first chemical tank 16a and/or the second chemical tank 16b can be made even smaller, the entire chlorine dioxide gas generator 100 can be miniaturized.

By supplying the gas discharge chambers 21 of the separation tank 20 with air before feeding the chemicals from the first chemical tank 16a and/or the second chemical tank 16b to the reactor as mentioned above, separation of the chlorine dioxide gas 30b can be initiated immediately after the chlorine dioxide solution 30a has been transported from the reactor 10.

Having finished the foregoing preparations, the chemicals are fed to the reactor by the chemical transporting pumps 16c in a 1:1 ratio, the chlorine dioxide solution 30a is produced in the reactor in the state described above, the chlorine dioxide gas 30b is separated from the chlorine dioxide solution 30a in the separation tank 20, and the separated chlorine dioxide gas 30b is gradually fed into the enclosed space 40. Under the foregoing conditions, it takes about 30 minutes to one hour until the concentration of the chlorine dioxide gas 30b in the enclosed space 40 becomes 400 ppm.

In order to sufficiently fumigate an enclosed space 40 having a capacity of 450 m$^3$, a state where the concentration of the chlorine dioxide gas 30b in the enclosed space 40 is 300 to 400 ppm needs to be maintained for about three hours. In order to do this, production of chlorine dioxide solution 30a may be carried out intermittently, by intermittently operating the chemical transporting pumps to feed the 25% sodium chlorite in the first chemical tank 16a and the 9% hydrochloric acid in the second chemical tank 16b into the reactor 10.

DESCRIPTION OF THE REFERENCE NUMERAL 100 chlorine dioxide gas generator
10 reactor
11 large cylinder
11a first connection port
11b second connection port
12 medium cylinder
12a collector
12b outlet
12c communication port
13 small cylinder
13a center cavity
13b connection port
14a first spiral groove
14b second spiral groove
15 lid
15a outlet
16a first chemical tank
16b second chemical tank
16c chemical transporting pump
20 separation tank
21 gas discharge chamber
22 drain pipe
23 liquid supply pipe
24 air supply pipe
24a inner pipe
24b outer pipe
24c upper outlet
24d lower outlet
24e air supply pipe
25 gas outlet
26 waste liquid chamber
26a gas outlet
27 partition wall
28 drain pipe
30a chlorine dioxide solution
30b chlorine dioxide gas
40 enclosed space
50 blower fan
60 control panel

What is claimed is:
1. A chlorine dioxide gas generator comprising:
a frame body which houses a first chemical tank which is filled with a first chemical containing chlorite, a second chemical tank which is filled with a second chemical containing acid, a reactor which causes a reaction between the first chemical containing chlorite and the second chemical containing acid, and a separation tank which separates a chlorine dioxide gas from a chlorine dioxide solution generated in the reactor, the chlorine dioxide gas generator being adapted to disinfect an enclosed space by means of the chlorine dioxide gas,
wherein the reactor comprises a large cylinder, a medium cylinder, a small cylinder, a first spiral groove between the large cylinder and the medium cylinder, a second spiral groove between the medium cylinder and the small cylinder, and a lid mounted to the large cylinder which sequentially houses the medium cylinder and the small cylinder,
wherein both of the chemicals supplied to a bottom of the large cylinder react with each other as they are supplied in order to the first spiral groove, the second spiral groove, and a center cavity of the small cylinder so that the chlorine dioxide solution can be generated,
wherein the separation tank comprises a plurality of vertically arranged gas discharge chambers, a plurality of drain pipes provided between the mutually adjacent gas discharge chambers, a liquid supply pipe which supplies the chlorine dioxide solution from the reactor to an uppermost gas discharge chamber, and an air supply pipe which feeds air into each of the gas discharge chambers, and wherein while the chlorine dioxide solution flows from the liquid supply pipe through the drain pipes into each gas discharge chamber, air is fed into each gas discharge chamber from the air supply pipe, and the chlorine dioxide gas is separated into the air within each gas discharge chamber.

2. The chlorine dioxide gas generator according to claim 1, further comprising a blower fan which forcibly feeds air from the enclosed space or outside air into the chlorine dioxide gas separated by the separation tank so as to dilute the chlorine dioxide gas.

* * * * *